US005554534A

United States Patent [19]

Michaels et al.

[11] Patent Number: 5,554,534

[45] Date of Patent: Sep. 10, 1996

[54] *BACILLUS THURINGIENSIS* TOXINS ACTIVE AGAINST SCARAB PESTS

[75] Inventors: Tracy E. Michaels, Ames, Iowa; Kenneth E. Narva, San Diego; Luis Foncerrada, Vista, both of Calif.

[73] Assignee: Mycogen Corporation, San Diego, Calif.

[21] Appl. No.: 315,468

[22] Filed: Sep. 30, 1994

Related U.S. Application Data

[60] Division of Ser. No. 14,941, Feb. 1, 1993, abandoned, which is a continuation-in-part of Ser. No. 828,430, Jan. 30, 1992, Pat. No. 5,185,148, which is a continuation-in-part of Ser. No. 808,316, Dec. 16, 1991, abandoned.

[51] Int. Cl.$^6$ .......... C12N 1/21; C12N 15/32; C07K 14/325

[52] U.S. Cl. .......... 435/252.3; 435/252.31; 536/23.71; 514/12

[58] Field of Search .......... 536/23.71; 514/12; 424/93.2, 93.461; 435/252.3, 252.31

[56] References Cited

U.S. PATENT DOCUMENTS

| | | | |
|---|---|---|---|
| 4,448,885 | 5/1984 | Schnepf et al. | 435/69.1 |
| 4,467,036 | 8/1984 | Schnepf et al. | 435/172.3 |
| 4,797,276 | 1/1989 | Herrnstadt et al. | 435/69.1 |
| 4,853,331 | 8/1989 | Herrnstadt et al. | 435/252.1 |
| 5,151,363 | 9/1992 | Payne | 435/252.5 |

FOREIGN PATENT DOCUMENTS

| | | |
|---|---|---|
| 2059242 | 7/1992 | Canada . |
| 0498537A2 | 12/1992 | European Pat. Off. . |
| WO92/19106 | 11/1992 | WIPO . |

OTHER PUBLICATIONS

Gaertner, F, L. Kim (1988) "Current Applied Recombinant DNA Projects" TIBTECH 6:S4–S7.

Gaertner, Frank (1990) "Cellular delivery ststems for insecticidal proteins: living and non–living microorganisms" Controlled Delivery of Crop–Protection Agents pp. 245–257.

Couch, T. L. (1980) "Mosquito Pathogenicity of *Bacillus thuringiensis* var. israelensis" Developments in Industrial Microbiology 22:61–67.

Beegle, C. C. (1978) "Use of Entomogenous Bacteria in Agroecosystems" Developments in Industrial Microbiology 20:97–104.

Krieg, V. A. et al. (1983) "*Bacillus thuringiensis* var. *tenebrionis*: ein neuer, gegenuber Larven von Coleopteren Wirksmaer Pathytyp" Z. ang. Ent. 96:500–508.

Hofte, H., H. R. Whiteley (1989) "Insecticidal Crystal Proteins of *Bacillus thuringiensis*" Microbiological Reviews 53(2):242–255.

Feitelson, J. S., J. Payne, L. Kim (1992) "*Bacillus thuringiensis:* Insects and Beyond" Bio/Technology 10:271–275.

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

*Primary Examiner*—Che S. Chereskin

*Attorney, Agent, or Firm*—Saliwanchik & Saliwanchik

[57] ABSTRACT

Certain isolates of *Bacillus thuringiensis* (*B.t.*) have been found to have activity against scarab pests. These isolates are designated *B.t.* PS86B1, *B.t.* PS43F and *B.t.* PS50C. These isolates, or transformed hosts containing the gene expressing a scarab-active toxin obtained from the isolates, can be used to control scarab-active pests, e.g., masked chafer, Cyclocephala sp., June beetle, Cotinis sp., northern masked chafer, *Cyclocephala borealis,* Japanese beetle, *Popillia japonica,* and Pasadena masked chafer, *Cyclocephala pasadenae,* in various environments.

4 Claims, No Drawings

SEQUENCE LISTING ( 1 ) GENERAL INFORMATION:

( i i i ) NUMBER OF SEQUENCES: 6

-continued ( 2 ) INFORMATION FOR SEQ ID NO:1:

( i ) SEQUENCE CHARACTERISTICS:
( A ) LENGTH: 3471 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: PS50C ( v i i ) IMMEDIATE SOURCE:
( A ) LIBRARY: LAMBDAGEM (TM) - 11 LIBRARY OF LUIS FONCERRADA
( B ) CLONE: 50C(a)

( x i ) SEQUENCE DESCRIPTION: SEQ ID NO:1:

ATGAGTCCAA ATAATCAAAA TGAATATGAA ATTATAGATG CGACACCTTC TACATCTGTA 60

TCCAGTGATT CTAACAGATA CCCTTTTGCG AATGAGCCAA CAGATGCGTT ACAAAATATG 120

AATTATAAAG ATTATCTGAA AATGTCTGGG GGAGAGAATC CTGAATTATT TGGAAATCCG 180

GAGACGTTTA TTAGTTCATC CACGATTCAA ACTGGAATTG GCATTGTTGG TCGAATACTA 240

GGAGCTTTAG GGGTTCCATT TGCTAGTCAG ATAGCTAGTT TCTATAGTTT CATTGTTGGT 300

CAATTATGGC CGTCAAAGAG CGTAGATATA TGGGGAGAAA TTATGGAACG AGTGGAAGAA 360

CTCGTTGATC AAAAAATAGA AAAATATGTA AAAGATAAGG CTCTTGCTGA ATTAAAAGGG 420

CTAGGAAATG CTTTGGATGT ATATCAGCAG TCACTTGAAG ATTGGCTGGA AAATCGCAAT 480

GATGCAAGAA CTAGAAGTGT TGTTTCTAAT CAATTTATAG CTTTAGATCT TAACTTTGTT 540

AGTTCAATTC CATCTTTTGC AGTATCCGGA CACGAAGTAC TATTATTAGC AGTATATGCA 600

CAGGCTGTGA ACCTACATTT ATTGTTATTA AGAGATGCTT CTATTTTTGG AGAAGAGTGG 660

GGATTTACAC CAGGTGAAAT TTCTAGATTT TATAATCGTC AAGTGCAACT TACCGCTGAA 720

TATTCAGACT ATTGTGTAAA GTGGTATAAA ATCGGCTTAG ATAAATTGAA AGGTACCACT 780

TCTAAAAGTT GGCTGAATTA TCATCAGTTC CGTAGAGAGA TGACATTACT GGTATTAGAT 840

TTGGTGGCGT TATTTCCAAA CTATGACACA CATATGTATC CAATCGAAAC AACAGCTCAA 900

CTTACACGGG ATGTGTATAC AGATCCGATA GCATTTAACA TAGTGACAAG TACTGGATTC 960

TGCAACCCTT GGTCAACCCA CAGTGGTATT CTTTTTTATG AAGTTGAAAA CAACGTAATT 1020

CGTCCGCCAC ACTTGTTTGA TATACTCAGC TCAGTAGAAA TTAATACAAG TAGAGGGGGT 1080

ATTACGTTAA ATAATGATGC ATATATAAAC TACTGGTCAG GACATACCCT AAAATATCGT 1140

AGAACAGCTG ATTCGACCGT AACATACACA GCTAATTACG GTCGAATCAC TTCAGAAAAG 1200

AATTCATTTG CACTTGAGGA TAGGGATATT TTTGAAATTA ATTCAACTGT GGCAAACCTA 1260

GCTAATTACT ACCAAAAGGC ATATGGTGTG CCGGGATCTT GGTTCCATAT GGTAAAAAGG 1320

GGAACCTCAT CAACAACAGC GTATTTATAT TCAAAAACAC ATACAGCTCT CCAAGGGTGT 1380

ACACAGGTTT ATGAATCAAG TGATGAAATA CCTCTAGATA GAACTGTACC GGTAGCTGAA 1440

AGCTATAGTC ATAGATTATC TCATATTACC TCCCATTCTT TCTCTAAAAA TGGGAGTGCA 1500

TACTATGGGA GTTTCCCTGT ATTTGTTTGG ACACATACTA GTGCGGATTT AAATAATACA 1560

-continued

```
ATATATTCAG ATAAAATCAC TCAAATTCCA GCGGTAAAGG GAGACATGTT ATATCTAGGG 1620
GGTTCCGTAG TACAGGGTCC TGGATTTACA GGAGGAGATA TATTAAAAAG AACCAATCCT 1680
AGCATATTAG GGACCTTTGC GGTTACAGTA AATGGGTCGT TATCACAAAG ATATCGTGTA 1740
AGAATTCGCT ATGCCTCTAC AACAGATTTT GAATTTACTC TATACCTTGG CGACACAATA 1800
GAAAAAAATA GATTTAACAA AACTATGGAT AATGGGGCAT CTTTAACGTA TGAAACATTT 1860
AAATTCGCAA GTTTCATTAC TGATTTCCAA TTCAGAGAAA CACAAGATAA AATACTCCTA 1920
TCCATGGGTG ATTTTAGCTC CGGTCAAGAA GTTTATATAG ACCGAATCGA ATTCATCCCA 1980
GTAGATGAGA CATATGAGGC GGAACAAGAT TTAGAAGCGG CGAAGAAAGC AGTGAATGCC 2040
TTGTTTACGA ATACAAAAGA TGGCTTACGA CCAGGTGTAA CGGATTATGA AGTAAATCAA 2100
GCGGCAAACT TAGTGGAATG CCTATCGGAT GATTTATATC CAAATGAAAA ACGATTGTTA 2160
TTTGATGCGG TGAGAGAGGC AAAACGCCTC AGTGGGGCAC GTAACTTACT ACAAGATCCA 2220
GATTTCCAAG AGATAAACGG AGAAAATGGA TGGGCGGCAA GTACGGGAAT TGAGATTGTA 2280
GAAGGGGATG CTGTATTTAA AGGACGTTAT CTACGCCTAC CAGGTGCACG AGAAATTGAT 2340
ACGGAAACGT ATCCAACGTA TCTGTATCAA AAAGTAGAGG AAGGTGTATT AAAACCATAC 2400
ACAAGATATA GACTGAGAGG GTTTGTGGGA AGTAGTCAAG GATTAGAAAT TTATACGATA 2460
CGTCACCAAA CGAATCGAAT TGTAAAGAAT GTACCAGATG ATTTATTGCC AGATGTATCT 2520
CCTGTAAACT CTGATGGCAG TATCAATCGA TGCAGCGAAC AAAAGTATGT GAATAGCCGT 2580
TTAGAAGGAG AAAACCGTTC TGGTGATGCA CATGAGTTCT CGCTCCCTAT CGATATAGGA 2640
GAGCTGGATT ACAATGAAAA TGCAGGAATA TGGGTTGGAT TTAAGATTAC GGACCCAGAG 2700
GGATACGCAA CACTTGGAAA TCTTGAATTA GTCGAAGAGG GACCTTTGTC AGGAGACGCA 2760
TTAGAGCGCT TGCAAAGAGA AGAACAACAG TGGAAGATTC AAATGACAAG AAGACGTGAA 2820
GAGACAGATA GAAGATACAT GGCATCGAAA CAAGCGGTAG ATCGTTTATA TGCCGATTAT 2880
CAGGATCAAC AACTGAATCC TGATGTAGAG ATTACAGATC TTACTGCGGC TCAAGATCTG 2940
ATACAGTCCA TTCCTTACGT ATATAACGAA ATGTTCCCAG AAATACCAGG GATGAACTAT 3000
ACGAAGTTTA CAGAATTAAC AGATCGACTC CAACAAGCGT GGAATTTGTA TGATCAGCGA 3060
AATGCCATAC CAAATGGTGA TTTTCGAAAT GGGTTAAGTA ATTGGAATGC AACGCCTGGC 3120
GTAGAAGTAC AACAAATCAA TCATACATCT GTCCTTGTGA TTCCAAACTG GGATGAACAA 3180
GTTTCACAAC AGTTTACAGT TCAACCGAAT CAAAGATATG TATTACGAGT TACTGCAAGA 3240
AAAGAAGGGG TAGGAAATGG ATATGTAAGT ATTCGTGATG GTGGAAATCA ATCAGAAACG 3300
CTTACTTTTA GTGCAAGCGA TTATGATACA AATGGTGTGT ATAATGACCA AACCGGCTAT 3360
ATCACAAAAA CAGTGACATT CATCCCGTAT ACAGATCAAA TGTGGATTGA AATAAGTGAA 3420
ACAGAAGGTA CGTTCTATAT AGAAAGTGTA GAATTGATTG TAGACGTAGA G 3471
```

( 2 ) INFORMATION FOR SEQ ID NO:2:

( i ) SEQUENCE CHARACTERISTICS:
( A ) LENGTH: 1157 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:

( A ) ORGANISM: Bacillus thuringiensis
( B ) STRAIN: kumamotoensis
( C ) INDIVIDUAL ISOLATE: PS50C ( v i i ) IMMEDIATE SOURCE:
( A ) LIBRARY: Lambdagem (TM) - 11 LIBRARY OF LUIS FONCERRADA
( B ) CLONE: 50C(a)

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ser | Pro | Asn | Asn | Gln | Asn | Glu | Tyr | Glu | Ile | Ile | Asp | Ala | Thr | Pro |
| 1 | | | | 5 | | | | | 10 | | | | | 15 | |
| Ser | Thr | Ser | Val | Ser | Ser | Asp | Ser | Asn | Arg | Tyr | Pro | Phe | Ala | Asn | Glu |
| | | | 20 | | | | | 25 | | | | | 30 | | |
| Pro | Thr | Asp | Ala | Leu | Gln | Asn | Met | Asn | Tyr | Lys | Asp | Tyr | Leu | Lys | Met |
| | | 35 | | | | | 40 | | | | | 45 | | | |
| Ser | Gly | Gly | Glu | Asn | Pro | Glu | Leu | Phe | Gly | Asn | Pro | Glu | Thr | Phe | Ile |
| | 50 | | | | | 55 | | | | | 60 | | | | |
| Ser | Ser | Ser | Thr | Ile | Gln | Thr | Gly | Ile | Gly | Ile | Val | Gly | Arg | Ile | Leu |
| 65 | | | | | 70 | | | | | 75 | | | | | 80 |
| Gly | Ala | Leu | Gly | Val | Pro | Phe | Ala | Ser | Gln | Ile | Ala | Ser | Phe | Tyr | Ser |
| | | | | 85 | | | | | 90 | | | | | 95 | |
| Phe | Ile | Val | Gly | Gln | Leu | Trp | Pro | Ser | Lys | Ser | Val | Asp | Ile | Trp | Gly |
| | | | 100 | | | | | 105 | | | | | 110 | | |
| Glu | Ile | Met | Glu | Arg | Val | Glu | Glu | Leu | Val | Asp | Gln | Lys | Ile | Glu | Lys |
| | | 115 | | | | | 120 | | | | | 125 | | | |
| Tyr | Val | Lys | Asp | Lys | Ala | Leu | Ala | Glu | Leu | Lys | Gly | Leu | Gly | Asn | Ala |
| | 130 | | | | | 135 | | | | | 140 | | | | |
| Leu | Asp | Val | Tyr | Gln | Gln | Ser | Leu | Glu | Asp | Trp | Leu | Glu | Asn | Arg | Asn |
| 145 | | | | | 150 | | | | | 155 | | | | | 160 |
| Asp | Ala | Arg | Thr | Arg | Ser | Val | Val | Ser | Asn | Gln | Phe | Ile | Ala | Leu | Asp |
| | | | | 165 | | | | | 170 | | | | | 175 | |
| Leu | Asn | Phe | Val | Ser | Ser | Ile | Pro | Ser | Phe | Ala | Val | Ser | Gly | His | Glu |
| | | | 180 | | | | | 185 | | | | | 190 | | |
| Val | Leu | Leu | Leu | Ala | Val | Tyr | Ala | Gln | Ala | Val | Asn | Leu | His | Leu | Leu |
| | | 195 | | | | | 200 | | | | | 205 | | | |
| Leu | Leu | Arg | Asp | Ala | Ser | Ile | Phe | Gly | Glu | Glu | Trp | Gly | Phe | Thr | Pro |
| | 210 | | | | | 215 | | | | | 220 | | | | |
| Gly | Glu | Ile | Ser | Arg | Phe | Tyr | Asn | Arg | Gln | Val | Gln | Leu | Thr | Ala | Glu |
| 225 | | | | | 230 | | | | | 235 | | | | | 240 |
| Tyr | Ser | Asp | Tyr | Cys | Val | Lys | Trp | Tyr | Lys | Ile | Gly | Leu | Asp | Lys | Leu |
| | | | | 245 | | | | | 250 | | | | | 255 | |
| Lys | Gly | Thr | Thr | Ser | Lys | Ser | Trp | Leu | Asn | Tyr | His | Gln | Phe | Arg | Arg |
| | | | 260 | | | | | 265 | | | | | 270 | | |
| Glu | Met | Thr | Leu | Leu | Val | Leu | Asp | Leu | Val | Ala | Leu | Phe | Pro | Asn | Tyr |
| | | 275 | | | | | 280 | | | | | 285 | | | |
| Asp | Thr | His | Met | Tyr | Pro | Ile | Glu | Thr | Thr | Ala | Gln | Leu | Thr | Arg | Asp |
| | 290 | | | | | 295 | | | | | 300 | | | | |
| Val | Tyr | Thr | Asp | Pro | Ile | Ala | Phe | Asn | Ile | Val | Thr | Ser | Thr | Gly | Phe |
| 305 | | | | | 310 | | | | | 315 | | | | | 320 |
| Cys | Asn | Pro | Trp | Ser | Thr | His | Ser | Gly | Ile | Leu | Phe | Tyr | Glu | Val | Glu |
| | | | | 325 | | | | | 330 | | | | | 335 | |
| Asn | Asn | Val | Ile | Arg | Pro | Pro | His | Leu | Phe | Asp | Ile | Leu | Ser | Ser | Val |
| | | | 340 | | | | | 345 | | | | | 350 | | |
| Glu | Ile | Asn | Thr | Ser | Arg | Gly | Gly | Ile | Thr | Leu | Asn | Asn | Asp | Ala | Tyr |
| | | 355 | | | | | 360 | | | | | 365 | | | |
| Ile | Asn | Tyr | Trp | Ser | Gly | His | Thr | Leu | Lys | Tyr | Arg | Arg | Thr | Ala | Asp |

-continued 370 375 380

Ser Thr Val Thr Tyr Thr Ala Asn Tyr Gly Arg Ile Thr Ser Glu Lys
385 390 395 400

Asn Ser Phe Ala Leu Glu Asp Arg Asp Ile Phe Glu Ile Asn Ser Thr
405 410 415

Val Ala Asn Leu Ala Asn Tyr Tyr Gln Lys Ala Tyr Gly Val Pro Gly
420 425 430

Ser Trp Phe His Met Val Lys Arg Gly Thr Ser Ser Thr Thr Ala Tyr
435 440 445

Leu Tyr Ser Lys Thr His Thr Ala Leu Gln Gly Cys Thr Gln Val Tyr
450 455 460

Glu Ser Ser Asp Glu Ile Pro Leu Asp Arg Thr Val Pro Val Ala Glu
465 470 475 480

Ser Tyr Ser His Arg Leu Ser His Ile Thr Ser His Ser Phe Ser Lys
485 490 495

Asn Gly Ser Ala Tyr Tyr Gly Ser Phe Pro Val Phe Val Trp Thr His
500 505 510

Thr Ser Ala Asp Leu Asn Asn Thr Ile Tyr Ser Asp Lys Ile Thr Gln
515 520 525

Ile Pro Ala Val Lys Gly Asp Met Leu Tyr Leu Gly Gly Ser Val Val
530 535 540

Gln Gly Pro Gly Phe Thr Gly Gly Asp Ile Leu Lys Arg Thr Asn Pro
545 550 555 560

Ser Ile Leu Gly Thr Phe Ala Val Thr Val Asn Gly Ser Leu Ser Gln
565 570 575

Arg Tyr Arg Val Arg Ile Arg Tyr Ala Ser Thr Thr Asp Phe Glu Phe
580 585 590

Thr Leu Tyr Leu Gly Asp Thr Ile Glu Lys Asn Arg Phe Asn Lys Thr
595 600 605

Met Asp Asn Gly Ala Ser Leu Thr Tyr Glu Thr Phe Lys Phe Ala Ser
610 615 620

Phe Ile Thr Asp Phe Gln Phe Arg Glu Thr Gln Asp Lys Ile Leu Leu
625 630 635 640

Ser Met Gly Asp Phe Ser Ser Gly Gln Glu Val Tyr Ile Asp Arg Ile
645 650 655

Glu Phe Ile Pro Val Asp Glu Thr Tyr Glu Ala Glu Gln Asp Leu Glu
660 665 670

Ala Ala Lys Lys Ala Val Asn Ala Leu Phe Thr Asn Thr Lys Asp Gly
675 680 685

Leu Arg Pro Gly Val Thr Asp Tyr Glu Val Asn Gln Ala Ala Asn Leu
690 695 700

Val Glu Cys Leu Ser Asp Asp Leu Tyr Pro Asn Glu Lys Arg Leu Leu
705 710 715 720

Phe Asp Ala Val Arg Glu Ala Lys Arg Leu Ser Gly Ala Arg Asn Leu
725 730 735

Leu Gln Asp Pro Asp Phe Gln Glu Ile Asn Gly Glu Asn Gly Trp Ala
740 745 750

Ala Ser Thr Gly Ile Glu Ile Val Glu Gly Asp Ala Val Phe Lys Gly
755 760 765

Arg Tyr Leu Arg Leu Pro Gly Ala Arg Glu Ile Asp Thr Glu Thr Tyr
770 775 780

Pro Thr Tyr Leu Tyr Gln Lys Val Glu Glu Gly Val Leu Lys Pro Tyr
785 790 795 800

-continued

| | | | | | | | | | | | | | | | |
|---|---|---|---|---|---|---|---|---|---|---|---|---|---|---|---|
| Thr | Arg | Tyr | Arg | Leu | Arg | Gly | Phe | Val | Gly | Ser | Ser | Gln | Gly | Leu | Glu |
| | | | | 805 | | | | | 810 | | | | | 815 | |
| Ile | Tyr | Thr | Ile | Arg | His | Gln | Thr | Asn | Arg | Ile | Val | Lys | Asn | Val | Pro |
| | | | 820 | | | | | 825 | | | | | 830 | | |
| Asp | Asp | Leu | Leu | Pro | Asp | Val | Ser | Pro | Val | Asn | Ser | Asp | Gly | Ser | Ile |
| | | 835 | | | | | 840 | | | | | 845 | | | |
| Asn | Arg | Cys | Ser | Glu | Gln | Lys | Tyr | Val | Asn | Ser | Arg | Leu | Glu | Gly | Glu |
| | 850 | | | | | 855 | | | | | 860 | | | | |
| Asn | Arg | Ser | Gly | Asp | Ala | His | Glu | Phe | Ser | Leu | Pro | Ile | Asp | Ile | Gly |
| 865 | | | | | 870 | | | | | 875 | | | | | 880 |
| Glu | Leu | Asp | Tyr | Asn | Glu | Asn | Ala | Gly | Ile | Trp | Val | Gly | Phe | Lys | Ile |
| | | | | 885 | | | | | 890 | | | | | 895 | |
| Thr | Asp | Pro | Glu | Gly | Tyr | Ala | Thr | Leu | Gly | Asn | Leu | Glu | Leu | Val | Glu |
| | | | 900 | | | | | 905 | | | | | 910 | | |
| Glu | Gly | Pro | Leu | Ser | Gly | Asp | Ala | Leu | Glu | Arg | Leu | Gln | Arg | Glu | Glu |
| | | 915 | | | | | 920 | | | | | 925 | | | |
| Gln | Gln | Trp | Lys | Ile | Gln | Met | Thr | Arg | Arg | Arg | Glu | Glu | Thr | Asp | Arg |
| | 930 | | | | | 935 | | | | | 940 | | | | |
| Arg | Tyr | Met | Ala | Ser | Lys | Gln | Ala | Val | Asp | Arg | Leu | Tyr | Ala | Asp | Tyr |
| 945 | | | | | 950 | | | | | 955 | | | | | 960 |
| Gln | Asp | Gln | Gln | Leu | Asn | Pro | Asp | Val | Glu | Ile | Thr | Asp | Leu | Thr | Ala |
| | | | | 965 | | | | | 970 | | | | | 975 | |
| Ala | Gln | Asp | Leu | Ile | Gln | Ser | Ile | Pro | Tyr | Val | Tyr | Asn | Glu | Met | Phe |
| | | | 980 | | | | | 985 | | | | | 990 | | |
| Pro | Glu | Ile | Pro | Gly | Met | Asn | Tyr | Thr | Lys | Phe | Thr | Glu | Leu | Thr | Asp |
| | | 995 | | | | | 1000 | | | | | 1005 | | | |
| Arg | Leu | Gln | Gln | Ala | Trp | Asn | Leu | Tyr | Asp | Gln | Arg | Asn | Ala | Ile | Pro |
| | 1010 | | | | | 1015 | | | | | 1020 | | | | |
| Asn | Gly | Asp | Phe | Arg | Asn | Gly | Leu | Ser | Asn | Trp | Asn | Ala | Thr | Pro | Gly |
| 1025 | | | | | 1030 | | | | | 1035 | | | | | 1040 |
| Val | Glu | Val | Gln | Gln | Ile | Asn | His | Thr | Ser | Val | Leu | Val | Ile | Pro | Asn |
| | | | | 1045 | | | | | 1050 | | | | | 1055 | |
| Trp | Asp | Glu | Gln | Val | Ser | Gln | Gln | Phe | Thr | Val | Gln | Pro | Asn | Gln | Arg |
| | | | 1060 | | | | | 1065 | | | | | 1070 | | |
| Tyr | Val | Leu | Arg | Val | Thr | Ala | Arg | Lys | Glu | Gly | Val | Gly | Asn | Gly | Tyr |
| | | 1075 | | | | | 1080 | | | | | 1085 | | | |
| Val | Ser | Ile | Arg | Asp | Gly | Gly | Asn | Gln | Ser | Glu | Thr | Leu | Thr | Phe | Ser |
| | 1090 | | | | | 1095 | | | | | 1100 | | | | |
| Ala | Ser | Asp | Tyr | Asp | Thr | Asn | Gly | Val | Tyr | Asn | Asp | Gln | Thr | Gly | Tyr |
| 1105 | | | | | 1110 | | | | | 1115 | | | | | 1120 |
| Ile | Thr | Lys | Thr | Val | Thr | Phe | Ile | Pro | Tyr | Thr | Asp | Gln | Met | Trp | Ile |
| | | | | 1125 | | | | | 1130 | | | | | 1135 | |
| Glu | Ile | Ser | Glu | Thr | Glu | Gly | Thr | Phe | Tyr | Ile | Glu | Ser | Val | Glu | Leu |
| | | | 1140 | | | | | 1145 | | | | | 1150 | | |
| Ile | Val | Asp | Val | Glu | | | | | | | | | | | |
| | | 1155 | | | | | | | | | | | | | |

( 2 ) INFORMATION FOR SEQ ID NO:3:

( i ) SEQUENCE CHARACTERISTICS:
( A ) LENGTH: 3507 base pairs
( B ) TYPE: nucleic acid
( C ) STRANDEDNESS: double
( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: 50C ( v i i ) IMMEDIATE SOURCE:
( A ) LIBRARY: LambdaGEM-11(tm) library of L. Foncerrada
( B ) CLONE: 50C(b)

( x i ) SEQUENCE DESCRIPTION: SEQ ID NO:3:

```
ATGAGTCCAA ATAATCAAAA TGAATATGAA ATTATAGATG CGACACCTTC TACATCTGTA   60
TCCAATGATT CTAACAGATA CCCTTTTGCG AATGAGCCAA CAAATGCGCT ACAAAATATG  120
GATTATAAAG ATTATTTAAA AATGTCTGCG GGAAATGTTA GTGAATACCC TGGTTCACCT  180
GAGGTATTTC TAAGCGAGCA AGATGCAGTT AAGGCCGCAA TTGATATAGT AGGTAAATTA  240
CTAACAGGTT TAGGGGTTCC ATTTGTTGGG CCGATAGTGA GTCTTTATAC TCAACTTATT  300
GATATTCTGT GGCCTTCAAA ACAAAAGAGT CAATGGGAAA TTTTTATGGA ACAAGTAGAA  360
GAACTCATTA ATCAAAAAAT AGCAGAATAT GCAAGGAATA AAGCGCTTTC GGAATTGGAA  420
GGGCTAGGGA ATAATTACCA ATTATATCTA ACTGCGCTTG AAGAGTGGAA AGAAAATCCA  480
AATGGTTCAA GAGCCTTACG AGATGTTCGA AATCGATTTG AAATCCTGGA TAGTTTATTT  540
ACGCAATATA TGCCATCTTT TCGAGTGACA AATTTTGAAG TACCATTCCT TACAGTATAT  600
ACAATGGCAG CAAACCTACA TTTACTTTTA TTAAGGGACG CATCAATTTT TGGAGAAGAA  660
TGGGGATTGT CTACAAGCAC TATTAATAAC TACTATAATC GTCAAATGAA ACTTACTGCA  720
GAATATTCTG ACCACTGTGT AAAGTGGTAT GAAACTGGTT TAGCAAAATT AAAAGGCTCG  780
AGCGCTAAAC AATGGATTGA CTATAACCAA TTCCGTAGAG AAATGACATT GACGGTGTTA  840
GACGTTGTTG CATTATTTTC AAACTATGAT ACGCGTACGT ATCCACTGGC AACAACAGCT  900
CAGCTTACAA GGGAAGTATA TACAGATCCA CTTGGCGCGG TAGATGTGCC TAATATTGGC  960
TCCTGGTATG ACAAAGCACC TTCTTTCTCA GAAATAGAAA AAGCGGCTAT TCGTCCACCT 1020
CATGTGTTTG ATTATATAAC GGGACTCACA GTTTATACAA AAAAACGTAG CTTCACTTCT 1080
GATCGTTATA TGAGATATTG GGCTGGTCAT CAAATAAGCT ATAAGCATAT CGGTACGAGT 1140
AGTACCTTTA CACAGATGTA TGGAACCAAT CAAAATTTAC AAAGTACTAG CAATTTTGAT 1200
TTTACGAATT ACGATATTTA CAAGACTTTA TCAAATGGTG CAGTACTCCT TGATATAGTT 1260
TACCCTGGTT ATACGTATAC ATTTTTTGGA ATGCCAGAAA CCGAGTTTTT TATGGTAAAT 1320
CAATTGAATA ATACCAGAAA GACGTTAACG TATAAACCAG CTTCCAAAGA TATTATAGAT 1380
CGGACAAGAG ATTCGGAATT AGAATTGCCT CCAGAAACTT CAGGTCAACC AAATTACGAG 1440
TCATATAGCC ATAGATTAGG TCATATTACA TTTATTTACT CCAGTTCAAC TAGCACGTAT 1500
GTACCTGTAT TTTCTTGGAC ACATCGGAGT GCAGATCTAA CAAATACAGT TAAAAGTGGC 1560
GAAATCACCC AAATACCAGG GGGCAAGTCT AGCACCATAG GCAGAAATAC TTATATAATA 1620
AAAGGGCGTG GTTATACAGG GGGAGACTTA GTGGCTTTAA CGGACCGCAT CGGAAGTTGT 1680
GAGTTTCAGA TGATCTTTCC AGAGTCTCAA CGATTCCGTA TTCGGATTCG TTACGCTTCT 1740
AATGAAACTA GTTATATTAG TTTATACGGA CTAAACCAAA GCGGAACTTT AAAATTCAAC 1800
CAGACATATT CTAATAAAAA TGAAAATGAT TTAACATATA ATGATTTCAA ATATATAGAA 1860
TATCCAAGAG TCATTTCAGT AAATGCTTCT TCAAACATAC AGAGGTTATC TATAGGTATA 1920
CAAACGAATA CAAATTTATT TATTTTAGAC CGAATCGAAT TCATCCCAGT AGATGAGACA 1980
```

-continued

```
TATGAAGCGG AAACGGATTT AGAAGCGGCA AAGAAAGCAG TGAATGCCTT GTTTACGAAT   2040
ACAAAAGATG GATTACAGCC AGGTGTAACG GATTATGAAG TAAATCAAGC GGCCAACTTA   2100
GTGGAATGCC TATCGGATGA TTTGTATCCA AATGAAAAAC GATTGTTATT TGATGCAGTG   2160
AGAGAGGCAA AACGACTTAG CGAGGCACGG AACTTACTAC AAGATCCAGA TTTCCAAGAG   2220
ATAAATGGAG AAAATGGATG GACGGCAAGT ACGGGAATTG AGGTTATAGA AGGGGATGCT   2280
GTATTCAAAG GGCGTTATCT ACGCCTACCA GGTGCGAGAG AAATAGATAC GGAAACGTAT   2340
CCAACGTATC TGTATCAAAA AGTAGAGGAA GGTGTATTAA AACCATACAC AAGGTATAGA   2400
CTGAGAGGAT TTGTGGGAAG TAGTCAAGGA TTAGAAATTT ATACGATTCG TCACCAAACG   2460
AATCGAATTG TAAAAAATGT ACCAGATGAT TTACTGCCAG ATGTACCTCC TGTAAACAAT   2520
GATGGTAGAA TCAATCGATG CAGCGAACAA AAGTATGTGA ATAGTCGTTT AGAAGTAGAA   2580
AACCGTTCTG GTGAAGCGCA TGAGTTCTCA ATCCCTATCG ATACAGGAGA GCTGGATTAC   2640
AATGAAAATG CAGGAATATG GGTTGGATTT AAGATTACGG ACCCAGAGGG ATACGCAACA   2700
CTTGGAAATC TTGAATTGGT CGAAGAGGGA CCTTTGTCAG GAGACGCATT AGAACGCTTG   2760
CAAAAAGAAG AACAACAGTG GAAGATTCAA ATGACAAGAA GACGTGAAGA GACAGATAGA   2820
AGATACATGG CATCGAAACA AGCGGTAGAT CGTTTATATG CCGATTATCA GGATCAGCAA   2880
CTGAATCCGA ATGTAGAGAT TACAGATCTT ACTGCGGCTC AAGATCTAAT ACAGTCCATT   2940
CCTTACGTGT ATAACGAAAT GTTCCCAGAA ATACCAGGAA TGAACTATAC GAAGTTTACA   3000
GAGTTAACAG ATCGACTCCA ACAAGCCTGG GGATTGTATG ATCAACGAAA CGCTATACCA   3060
AATGGAGATT ACCGAAATGA ATTAAGTAAT TGGAATACAA CATCTGGTGT GAATGTACAA   3120
CAAATCAATC ATACATCTGT CCTTGTGATT CCAAACTGGA ATGAACAAGT TTCACAAAAG   3180
TTTACAGTTC AACCGAATCA AAGATATGTG TTACGAGTTA CTGCAAGAAA AGAAGGGGTA   3240
GGAAATGGAT ATGTAAGTAT TCGTGATGGT GGAAATCAAT CAGAAACGCT TACTTTTAGT   3300
GCAAGCGATT ATGATACAAA TGGTATGTAT GATACACAAG CGTCGAATAC AAACGGATAT   3360
AACACAAATA GTGTGTACAT GATCAAACCG GCTATATCAC GAAAAACAGT GGACATTTCA   3420
TCCGTATACA ATCAAATGTG GATTGAGATA AGTGAGACAG AAGGTACGTT CTATATAGAA   3480
AGTGTAGAAT TGATTGTAGA CGTAGAG                                       3507
```

( 2 ) INFORMATION FOR SEQ ID NO:4:

( i ) SEQUENCE CHARACTERISTICS:
( A ) LENGTH: 1169 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: 50C ( v i i ) IMMEDIATE SOURCE:
( A ) LIBRARY: LambdaGEM-11 library of L. Foncerrada
( B ) CLONE: 50C(b)

( x i ) SEQUENCE DESCRIPTION: SEQ ID NO:4:

Met Ser Pro Asn Asn Gln Asn Glu Tyr Glu Ile Ile Asp Ala Thr Pro

-continued

| 1 | | | | 5 | | | | | 10 | | | | | 15 | |
|---|---|---|---|---|---|---|---|---|---|---|---|---|---|---|---|
| Ser | Thr | Ser | Val | Ser | Asn | Asp | Ser | Asn | Arg | Tyr | Pro | Phe | Ala | Asn | Glu |
| | | | 20 | | | | | 25 | | | | | 30 | | |
| Pro | Thr | Asn | Ala | Leu | Gln | Asn | Met | Asp | Tyr | Lys | Asp | Tyr | Leu | Lys | Met |
| | | 35 | | | | | 40 | | | | | 45 | | | |
| Ser | Ala | Gly | Asn | Val | Ser | Glu | Tyr | Pro | Gly | Ser | Pro | Glu | Val | Phe | Leu |
| | 50 | | | | | 55 | | | | | 60 | | | | |
| Ser | Glu | Gln | Asp | Ala | Val | Lys | Ala | Ala | Ile | Asp | Ile | Val | Gly | Lys | Leu |
| 65 | | | | | 70 | | | | | 75 | | | | | 80 |
| Leu | Thr | Gly | Leu | Gly | Val | Pro | Phe | Val | Gly | Pro | Ile | Val | Ser | Leu | Tyr |
| | | | | 85 | | | | | 90 | | | | | 95 | |
| Thr | Gln | Leu | Ile | Asp | Ile | Leu | Trp | Pro | Ser | Lys | Gln | Lys | Ser | Gln | Trp |
| | | | 100 | | | | | 105 | | | | | 110 | | |
| Glu | Ile | Phe | Met | Glu | Gln | Val | Glu | Glu | Leu | Ile | Asn | Gln | Lys | Ile | Ala |
| | | 115 | | | | | 120 | | | | | 125 | | | |
| Glu | Tyr | Ala | Arg | Asn | Lys | Ala | Leu | Ser | Glu | Leu | Glu | Gly | Leu | Gly | Asn |
| | 130 | | | | | 135 | | | | | 140 | | | | |
| Asn | Tyr | Gln | Leu | Tyr | Leu | Thr | Ala | Leu | Glu | Glu | Trp | Lys | Glu | Asn | Pro |
| 145 | | | | | 150 | | | | | 155 | | | | | 160 |
| Asn | Gly | Ser | Arg | Ala | Leu | Arg | Asp | Val | Arg | Asn | Arg | Phe | Glu | Ile | Leu |
| | | | | 165 | | | | | 170 | | | | | 175 | |
| Asp | Ser | Leu | Phe | Thr | Gln | Tyr | Met | Pro | Ser | Phe | Arg | Val | Thr | Asn | Phe |
| | | | 180 | | | | | 185 | | | | | 190 | | |
| Glu | Val | Pro | Phe | Leu | Thr | Val | Tyr | Thr | Met | Ala | Ala | Asn | Leu | His | Leu |
| | | 195 | | | | | 200 | | | | | 205 | | | |
| Leu | Leu | Leu | Arg | Asp | Ala | Ser | Ile | Phe | Gly | Glu | Glu | Trp | Gly | Leu | Ser |
| | 210 | | | | | 215 | | | | | 220 | | | | |
| Thr | Ser | Thr | Ile | Asn | Asn | Tyr | Tyr | Asn | Arg | Gln | Met | Lys | Leu | Thr | Ala |
| 225 | | | | | 230 | | | | | 235 | | | | | 240 |
| Glu | Tyr | Ser | Asp | His | Cys | Val | Lys | Trp | Tyr | Glu | Thr | Gly | Leu | Ala | Lys |
| | | | | 245 | | | | | 250 | | | | | 255 | |
| Leu | Lys | Gly | Ser | Ser | Ala | Lys | Gln | Trp | Ile | Asp | Tyr | Asn | Gln | Phe | Arg |
| | | | 260 | | | | | 265 | | | | | 270 | | |
| Arg | Glu | Met | Thr | Leu | Thr | Val | Leu | Asp | Val | Val | Ala | Leu | Phe | Ser | Asn |
| | | 275 | | | | | 280 | | | | | 285 | | | |
| Tyr | Asp | Thr | Arg | Thr | Tyr | Pro | Leu | Ala | Thr | Thr | Ala | Gln | Leu | Thr | Arg |
| | 290 | | | | | 295 | | | | | 300 | | | | |
| Glu | Val | Tyr | Thr | Asp | Pro | Leu | Gly | Ala | Val | Asp | Val | Pro | Asn | Ile | Gly |
| 305 | | | | | 310 | | | | | 315 | | | | | 320 |
| Ser | Trp | Tyr | Asp | Lys | Ala | Pro | Ser | Phe | Ser | Glu | Ile | Glu | Lys | Ala | Ala |
| | | | | 325 | | | | | 330 | | | | | 335 | |
| Ile | Arg | Pro | Pro | His | Val | Phe | Asp | Tyr | Ile | Thr | Gly | Leu | Thr | Val | Tyr |
| | | | 340 | | | | | 345 | | | | | 350 | | |
| Thr | Lys | Lys | Arg | Ser | Phe | Thr | Ser | Asp | Arg | Tyr | Met | Arg | Tyr | Trp | Ala |
| | | 355 | | | | | 360 | | | | | 365 | | | |
| Gly | His | Gln | Ile | Ser | Tyr | Lys | His | Ile | Gly | Thr | Ser | Ser | Thr | Phe | Thr |
| | 370 | | | | | 375 | | | | | 380 | | | | |
| Gln | Met | Tyr | Gly | Thr | Asn | Gln | Asn | Leu | Gln | Ser | Thr | Ser | Asn | Phe | Asp |
| 385 | | | | | 390 | | | | | 395 | | | | | 400 |
| Phe | Thr | Asn | Tyr | Asp | Ile | Tyr | Lys | Thr | Leu | Ser | Asn | Gly | Ala | Val | Leu |
| | | | | 405 | | | | | 410 | | | | | 415 | |
| Leu | Asp | Ile | Val | Tyr | Pro | Gly | Tyr | Thr | Tyr | Thr | Phe | Phe | Gly | Met | Pro |
| | | | 420 | | | | | 425 | | | | | 430 | | |

-continued

| | | | | | | | | | | | | | | | |
|---|---|---|---|---|---|---|---|---|---|---|---|---|---|---|---|
| Glu | Thr | Glu | Phe | Phe | Met | Val | Asn | Gln | Leu | Asn | Asn | Thr | Arg | Lys | Thr |
| | | 435 | | | | | 440 | | | | | 445 | | | |
| Leu | Thr | Tyr | Lys | Pro | Ala | Ser | Lys | Asp | Ile | Ile | Asp | Arg | Thr | Arg | Asp |
| | 450 | | | | | 455 | | | | | 460 | | | | |
| Ser | Glu | Leu | Glu | Leu | Pro | Pro | Glu | Thr | Ser | Gly | Gln | Pro | Asn | Tyr | Glu |
| 465 | | | | | 470 | | | | | 475 | | | | | 480 |
| Ser | Tyr | Ser | His | Arg | Leu | Gly | His | Ile | Thr | Phe | Ile | Tyr | Ser | Ser | Ser |
| | | | | 485 | | | | | 490 | | | | | 495 | |
| Thr | Ser | Thr | Tyr | Val | Pro | Val | Phe | Ser | Trp | Thr | His | Arg | Ser | Ala | Asp |
| | | | 500 | | | | | 505 | | | | | 510 | | |
| Leu | Thr | Asn | Thr | Val | Lys | Ser | Gly | Glu | Ile | Thr | Gln | Ile | Pro | Gly | Gly |
| | | 515 | | | | | 520 | | | | | 525 | | | |
| Lys | Ser | Ser | Thr | Ile | Gly | Arg | Asn | Thr | Tyr | Ile | Ile | Lys | Gly | Arg | Gly |
| | 530 | | | | | 535 | | | | | 540 | | | | |
| Tyr | Thr | Gly | Gly | Asp | Leu | Val | Ala | Leu | Thr | Asp | Arg | Ile | Gly | Ser | Cys |
| 545 | | | | | 550 | | | | | 555 | | | | | 560 |
| Glu | Phe | Gln | Met | Ile | Phe | Pro | Glu | Ser | Gln | Arg | Phe | Arg | Ile | Arg | Ile |
| | | | | 565 | | | | | 570 | | | | | 575 | |
| Arg | Tyr | Ala | Ser | Asn | Glu | Thr | Ser | Tyr | Ile | Ser | Leu | Tyr | Gly | Leu | Asn |
| | | | 580 | | | | | 585 | | | | | 590 | | |
| Gln | Ser | Gly | Thr | Leu | Lys | Phe | Asn | Gln | Thr | Tyr | Ser | Asn | Lys | Asn | Glu |
| | | 595 | | | | | 600 | | | | | 605 | | | |
| Asn | Asp | Leu | Thr | Tyr | Asn | Asp | Phe | Lys | Tyr | Ile | Glu | Tyr | Pro | Arg | Val |
| | 610 | | | | | 615 | | | | | 620 | | | | |
| Ile | Ser | Val | Asn | Ala | Ser | Ser | Asn | Ile | Gln | Arg | Leu | Ser | Ile | Gly | Ile |
| 625 | | | | | 630 | | | | | 635 | | | | | 640 |
| Gln | Thr | Asn | Thr | Asn | Leu | Phe | Ile | Leu | Asp | Arg | Ile | Glu | Phe | Ile | Pro |
| | | | | 645 | | | | | 650 | | | | | 655 | |
| Val | Asp | Glu | Thr | Tyr | Glu | Ala | Glu | Thr | Asp | Leu | Glu | Ala | Ala | Lys | Lys |
| | | | 660 | | | | | 665 | | | | | 670 | | |
| Ala | Val | Asn | Ala | Leu | Phe | Thr | Asn | Thr | Lys | Asp | Gly | Leu | Gln | Pro | Gly |
| | | 675 | | | | | 680 | | | | | 685 | | | |
| Val | Thr | Asp | Tyr | Glu | Val | Asn | Gln | Ala | Ala | Asn | Leu | Val | Glu | Cys | Leu |
| | 690 | | | | | 695 | | | | | 700 | | | | |
| Ser | Asp | Asp | Leu | Tyr | Pro | Asn | Glu | Lys | Arg | Leu | Leu | Phe | Asp | Ala | Val |
| 705 | | | | | 710 | | | | | 715 | | | | | 720 |
| Arg | Glu | Ala | Lys | Arg | Leu | Ser | Glu | Ala | Arg | Asn | Leu | Leu | Gln | Asp | Pro |
| | | | | 725 | | | | | 730 | | | | | 735 | |
| Asp | Phe | Gln | Glu | Ile | Asn | Gly | Glu | Asn | Gly | Trp | Thr | Ala | Ser | Thr | Gly |
| | | | 740 | | | | | 745 | | | | | 750 | | |
| Ile | Glu | Val | Ile | Glu | Gly | Asp | Ala | Val | Phe | Lys | Gly | Arg | Tyr | Leu | Arg |
| | | 755 | | | | | 760 | | | | | 765 | | | |
| Leu | Pro | Gly | Ala | Arg | Glu | Ile | Asp | Thr | Glu | Thr | Tyr | Pro | Thr | Tyr | Leu |
| | 770 | | | | | 775 | | | | | 780 | | | | |
| Tyr | Gln | Lys | Val | Glu | Glu | Gly | Val | Leu | Lys | Pro | Tyr | Thr | Arg | Tyr | Arg |
| 785 | | | | | 790 | | | | | 795 | | | | | 800 |
| Leu | Arg | Gly | Phe | Val | Gly | Ser | Ser | Gln | Gly | Leu | Glu | Ile | Tyr | Thr | Ile |
| | | | | 805 | | | | | 810 | | | | | 815 | |
| Arg | His | Gln | Thr | Asn | Arg | Ile | Val | Lys | Asn | Val | Pro | Asp | Asp | Leu | Leu |
| | | | 820 | | | | | 825 | | | | | 830 | | |
| Pro | Asp | Val | Pro | Pro | Val | Asn | Asn | Asp | Gly | Arg | Ile | Asn | Arg | Cys | Ser |
| | | 835 | | | | | 840 | | | | | 845 | | | |
| Glu | Gln | Lys | Tyr | Val | Asn | Ser | Arg | Leu | Glu | Val | Glu | Asn | Arg | Ser | Gly |
| | 850 | | | | | 855 | | | | | 860 | | | | |

-continued

Glu Ala His Glu Phe Ser Ile Pro Ile Asp Thr Gly Glu Leu Asp Tyr
865 870 875 880

Asn Glu Asn Ala Gly Ile Trp Val Gly Phe Lys Ile Thr Asp Pro Glu
885 890 895

Gly Tyr Ala Thr Leu Gly Asn Leu Glu Leu Val Glu Glu Gly Pro Leu
900 905 910

Ser Gly Asp Ala Leu Glu Arg Leu Gln Lys Glu Glu Gln Gln Trp Lys
915 920 925

Ile Gln Met Thr Arg Arg Arg Glu Glu Thr Asp Arg Arg Tyr Met Ala
930 935 940

Ser Lys Gln Ala Val Asp Arg Leu Tyr Ala Asp Tyr Gln Asp Gln Gln
945 950 955 960

Leu Asn Pro Asn Val Glu Ile Thr Asp Leu Thr Ala Ala Gln Asp Leu
965 970 975

Ile Gln Ser Ile Pro Tyr Val Tyr Asn Glu Met Phe Pro Glu Ile Pro
980 985 990

Gly Met Asn Tyr Thr Lys Phe Thr Glu Leu Thr Asp Arg Leu Gln Gln
995 1000 1005

Ala Trp Gly Leu Tyr Asp Gln Arg Asn Ala Ile Pro Asn Gly Asp Tyr
1010 1015 1020

Arg Asn Glu Leu Ser Asn Trp Asn Thr Thr Ser Gly Val Asn Val Gln
1025 1030 1035 1040

Gln Ile Asn His Thr Ser Val Leu Val Ile Pro Asn Trp Asn Glu Gln
1045 1050 1055

Val Ser Gln Lys Phe Thr Val Gln Pro Asn Gln Arg Tyr Val Leu Arg
1060 1065 1070

Val Thr Ala Arg Lys Glu Gly Val Gly Asn Gly Tyr Val Ser Ile Arg
1075 1080 1085

Asp Gly Gly Asn Gln Ser Glu Thr Leu Thr Phe Ser Ala Ser Asp Tyr
1090 1095 1100

Asp Thr Asn Gly Met Tyr Asp Thr Gln Ala Ser Asn Thr Asn Gly Tyr
1105 1110 1115 1120

Asn Thr Asn Ser Val Tyr Met Ile Lys Pro Ala Ile Ser Arg Lys Thr
1125 1130 1135

Val Asp Ile Ser Ser Val Tyr Asn Gln Met Trp Ile Glu Ile Ser Glu
1140 1145 1150

Thr Glu Gly Thr Phe Tyr Ile Glu Ser Val Glu Leu Ile Val Asp Val
1155 1160 1165

Glu ( 2 ) INFORMATION FOR SEQ ID NO:5:

( i ) SEQUENCE CHARACTERISTICS:
( A ) LENGTH: 1953 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: tolworthi
( C ) INDIVIDUAL ISOLATE: 43F -continued ( v i i ) IMMEDIATE SOURCE:
( B ) CLONE: E. coli XL1-Blue (pM1,98- 4), NRRL B-18291

( i x ) FEATURE:
( A ) NAME/KEY: CDS
( B ) LOCATION: 1..1953

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG | AAT | CCA | AAC | AAT | CGA | AGT | GAA | TAT | GAT | ACG | ATA | AAG | GTT | ACA | CCT | 48 |
| Met | Asn | Pro | Asn | Asn | Arg | Ser | Glu | Tyr | Asp | Thr | Ile | Lys | Val | Thr | Pro | |
| 1 | | | | 5 | | | | | 10 | | | | | 15 | | |
| AAC | AGT | GAA | TTG | CCA | ACT | AAC | CAT | AAT | CAA | TAT | CCT | TTA | GCT | GAC | AAT | 96 |
| Asn | Ser | Glu | Leu | Pro | Thr | Asn | His | Asn | Gln | Tyr | Pro | Leu | Ala | Asp | Asn | |
| | | | 20 | | | | | 25 | | | | | 30 | | | |
| CCA | AAT | TCG | ACA | CTA | GAA | GAA | TTA | AAT | TAT | AAA | GAA | TTT | TTA | AGA | ATG | 144 |
| Pro | Asn | Ser | Thr | Leu | Glu | Glu | Leu | Asn | Tyr | Lys | Glu | Phe | Leu | Arg | Met | |
| | | 35 | | | | | 40 | | | | | 45 | | | | |
| ACT | GCA | GAC | AAT | TCT | ACG | GAA | GTG | CTA | GAC | AGC | TCT | ACA | GTA | AAA | GAT | 192 |
| Thr | Ala | Asp | Asn | Ser | Thr | Glu | Val | Leu | Asp | Ser | Ser | Thr | Val | Lys | Asp | |
| | 50 | | | | | 55 | | | | | 60 | | | | | |
| GCA | GTT | GGG | ACA | GGA | ATT | TCT | GTT | GTA | GGA | CAG | ATT | TTA | GGT | GTT | GTA | 240 |
| Ala | Val | Gly | Thr | Gly | Ile | Ser | Val | Val | Gly | Gln | Ile | Leu | Gly | Val | Val | |
| 65 | | | | | 70 | | | | | 75 | | | | | 80 | |
| GGG | GTT | CCA | TTT | GCT | GGG | GCG | CTC | ACT | TCA | TTT | TAT | CAA | TCA | TTT | CTT | 288 |
| Gly | Val | Pro | Phe | Ala | Gly | Ala | Leu | Thr | Ser | Phe | Tyr | Gln | Ser | Phe | Leu | |
| | | | | 85 | | | | | 90 | | | | | 95 | | |
| AAC | GCT | ATA | TGG | CCA | AGT | GAT | GCT | GAC | CCA | TGG | AAG | GCT | TTT | ATG | GCA | 336 |
| Asn | Ala | Ile | Trp | Pro | Ser | Asp | Ala | Asp | Pro | Trp | Lys | Ala | Phe | Met | Ala | |
| | | | 100 | | | | | 105 | | | | | 110 | | | |
| CAA | GTG | GAA | GTA | CTG | ATA | GAT | AAG | AAA | ATA | GAG | GAG | TAT | GCT | AAA | AGT | 384 |
| Gln | Val | Glu | Val | Leu | Ile | Asp | Lys | Lys | Ile | Glu | Glu | Tyr | Ala | Lys | Ser | |
| | | 115 | | | | | 120 | | | | | 125 | | | | |
| AAA | GCT | CTT | GCA | GAG | TTA | CAG | GGT | CTT | CAA | AAT | AAT | TTT | GAA | GAT | TAT | 432 |
| Lys | Ala | Leu | Ala | Glu | Leu | Gln | Gly | Leu | Gln | Asn | Asn | Phe | Glu | Asp | Tyr | |
| | 130 | | | | | 135 | | | | | 140 | | | | | |
| GTA | AAT | GCG | TTG | GAT | TCC | TGG | AAG | AAA | GCG | CCT | GTA | AAT | TTA | CGA | AGT | 480 |
| Val | Asn | Ala | Leu | Asp | Ser | Trp | Lys | Lys | Ala | Pro | Val | Asn | Leu | Arg | Ser | |
| 145 | | | | | 150 | | | | | 155 | | | | | 160 | |
| CGA | AGA | AGC | CAA | GAT | CGA | ATA | AGA | GAA | CTT | TTT | TCT | CAA | GCA | GAA | AGC | 528 |
| Arg | Arg | Ser | Gln | Asp | Arg | Ile | Arg | Glu | Leu | Phe | Ser | Gln | Ala | Glu | Ser | |
| | | | | 165 | | | | | 170 | | | | | 175 | | |
| CAT | TTT | CGT | AAT | TCC | ATG | CCG | TCA | TTT | GCG | GTT | TCC | AAA | TTC | GAA | GTT | 576 |
| His | Phe | Arg | Asn | Ser | Met | Pro | Ser | Phe | Ala | Val | Ser | Lys | Phe | Glu | Val | |
| | | | 180 | | | | | 185 | | | | | 190 | | | |
| CTG | TTT | CTA | CCA | ACA | TAT | GCA | CAA | GCT | GCA | AAT | ACA | CAT | TTA | TTG | CTA | 624 |
| Leu | Phe | Leu | Pro | Thr | Tyr | Ala | Gln | Ala | Ala | Asn | Thr | His | Leu | Leu | Leu | |
| | | 195 | | | | | 200 | | | | | 205 | | | | |
| TTA | AAA | GAT | GCT | CAA | GTT | TTT | GGA | GAA | GAA | TGG | GGA | TAT | TCT | TCA | GAA | 672 |
| Leu | Lys | Asp | Ala | Gln | Val | Phe | Gly | Glu | Glu | Trp | Gly | Tyr | Ser | Ser | Glu | |
| | 210 | | | | | 215 | | | | | 220 | | | | | |
| GAT | ATT | GCT | GAA | TTT | TAT | CAA | AGA | CAA | TTA | AAA | CTT | ACG | CAA | CAA | TAC | 720 |
| Asp | Ile | Ala | Glu | Phe | Tyr | Gln | Arg | Gln | Leu | Lys | Leu | Thr | Gln | Gln | Tyr | |
| 225 | | | | | 230 | | | | | 235 | | | | | 240 | |
| ACT | GAC | CAT | TGT | GTC | AAT | TGG | TAT | AAT | GTT | GGA | TTA | AAT | AGT | TTA | AGA | 768 |
| Thr | Asp | His | Cys | Val | Asn | Trp | Tyr | Asn | Val | Gly | Leu | Asn | Ser | Leu | Arg | |
| | | | | 245 | | | | | 250 | | | | | 255 | | |
| GGT | TCA | ACT | TAT | GAT | GCA | TGG | GTC | AAA | TTT | AAC | CGT | TTT | CGC | AGA | GAA | 816 |
| Gly | Ser | Thr | Tyr | Asp | Ala | Trp | Val | Lys | Phe | Asn | Arg | Phe | Arg | Arg | Glu | |
| | | | 260 | | | | | 265 | | | | | 270 | | | |
| ATG | ACA | TTA | ACT | GTA | TTA | GAT | CTA | ATT | GTA | TTA | TTC | CCA | TTT | TAT | GAT | 864 |
| Met | Thr | Leu | Thr | Val | Leu | Asp | Leu | Ile | Val | Leu | Phe | Pro | Phe | Tyr | Asp | |
| | | 275 | | | | | 280 | | | | | 285 | | | | |

-continued

GTT CGG TTA TAC TCA AAA GGA GTT AAA ACA GAA CTA ACA AGA GAC ATT 912
Val Arg Leu Tyr Ser Lys Gly Val Lys Thr Glu Leu Thr Arg Asp Ile
290 295 300

TTT ACA GAT CCA ATT TTT ACA CTC AAT GCT CTT CAA GAG TAT GGA CCA 960
Phe Thr Asp Pro Ile Phe Thr Leu Asn Ala Leu Gln Glu Tyr Gly Pro
305 310 315 320

ACT TTT TCG AGT ATA GAA AAC TCT ATT CGA AAA CCT CAT TTA TTT GAT 1008
Thr Phe Ser Ser Ile Glu Asn Ser Ile Arg Lys Pro His Leu Phe Asp
325 330 335

TAT TTG CGT GGG ATT GAA TTT CAT ACG CGT CTT CGA CCT GGT TAC TCT 1056
Tyr Leu Arg Gly Ile Glu Phe His Thr Arg Leu Arg Pro Gly Tyr Ser
340 345 350

GGG AAA GAT TCT TTC AAT TAT TGG TCT GGT AAT TAT GTA GAA ACT AGA 1104
Gly Lys Asp Ser Phe Asn Tyr Trp Ser Gly Asn Tyr Val Glu Thr Arg
355 360 365

CCT AGT ATA GGA TCT AAT GAT ACA ATC ACT TCC CCA TTT TAT GGA GAT 1152
Pro Ser Ile Gly Ser Asn Asp Thr Ile Thr Ser Pro Phe Tyr Gly Asp
370 375 380

AAA TCT ATT GAA CCT ATA CAA AAG CTA AGC TTT GAT GGA CAA AAA GTT 1200
Lys Ser Ile Glu Pro Ile Gln Lys Leu Ser Phe Asp Gly Gln Lys Val
385 390 395 400

TAT CGA ACT ATA GCT AAT ACA GAC ATA GCG GCT TTT CCG GAT GGC AAG 1248
Tyr Arg Thr Ile Ala Asn Thr Asp Ile Ala Ala Phe Pro Asp Gly Lys
405 410 415

ATA TAT TTT GGT GTT ACG AAA GTT GAT TTT AGT CAA TAT GAT GAT CAA 1296
Ile Tyr Phe Gly Val Thr Lys Val Asp Phe Ser Gln Tyr Asp Asp Gln
420 425 430

AAA AAT GAA ACT AGT ACA CAA ACA TAT GAT TCA AAA AGA TAC AAT GGC 1344
Lys Asn Glu Thr Ser Thr Gln Thr Tyr Asp Ser Lys Arg Tyr Asn Gly
435 440 445

TAT TTA GGT GCA CAG GAT TCT ATC GAC CAA TTA CCA CCA GAA ACA ACA 1392
Tyr Leu Gly Ala Gln Asp Ser Ile Asp Gln Leu Pro Pro Glu Thr Thr
450 455 460

GAT GAA CCA CTT GAA AAA GCA TAT AGT CAT CAG CTT AAT TAC GCA GAA 1440
Asp Glu Pro Leu Glu Lys Ala Tyr Ser His Gln Leu Asn Tyr Ala Glu
465 470 475 480

TGT TTC TTA ATG CAG GAC CGT CGT GGA ACA ATT CCA TTT TTT ACT TGG 1488
Cys Phe Leu Met Gln Asp Arg Arg Gly Thr Ile Pro Phe Phe Thr Trp
485 490 495

ACA CAT AGA AGT GTA GAC TTT TTT AAT ACA ATT GAT GCT GAA AAA ATT 1536
Thr His Arg Ser Val Asp Phe Phe Asn Thr Ile Asp Ala Glu Lys Ile
500 505 510

ACT CAA CTT CCA GTA GTG AAA GCA TAT GCC TTG TCT TCA GGC GCT TCC 1584
Thr Gln Leu Pro Val Val Lys Ala Tyr Ala Leu Ser Ser Gly Ala Ser
515 520 525

ATT ATT GAA GGT CCA GGA TTC ACA GGA GGA AAT TTA CTA TTC CTA AAA 1632
Ile Ile Glu Gly Pro Gly Phe Thr Gly Gly Asn Leu Leu Phe Leu Lys
530 535 540

GAA TCT AGT AAT TCA ATT GCT AAA TTT AAA GTT ACC TTA AAT TCA GCA 1680
Glu Ser Ser Asn Ser Ile Ala Lys Phe Lys Val Thr Leu Asn Ser Ala
545 550 555 560

GCC TTG TTA CAA CGA TAT CGC GTA AGA ATA CGC TAT GCT TCA ACC ACT 1728
Ala Leu Leu Gln Arg Tyr Arg Val Arg Ile Arg Tyr Ala Ser Thr Thr
565 570 575

AAC CTA CGA CTT TTC GTG CAA AAT TCA AAC AAT GAT TTT CTT GTC ATC 1776
Asn Leu Arg Leu Phe Val Gln Asn Ser Asn Asn Asp Phe Leu Val Ile
580 585 590

TAC ATT AAT AAA ACT ATG AAT ATA GAT GGT GAT TTA ACA TAT CAA ACA 1824
Tyr Ile Asn Lys Thr Met Asn Ile Asp Gly Asp Leu Thr Tyr Gln Thr
595 600 605

-continued

TTT GAT TTC GCA ACT AGT AAT TCT AAT ATG GGA TTC TCT GGT GAT ACA 1872
Phe Asp Phe Ala Thr Ser Asn Ser Asn Met Gly Phe Ser Gly Asp Thr
610 615 620

AAT GAC TTT ATA ATA GGA GCA GAA TCT TTC GTT TCT AAT GAA AAA ATC 1920
Asn Asp Phe Ile Ile Gly Ala Glu Ser Phe Val Ser Asn Glu Lys Ile
625 630 635 640

TAT ATA GAT AAG ATA GAA TTT ATC CCA GTA CAA 1953
Tyr Ile Asp Lys Ile Glu Phe Ile Pro Val Gln
645 650

( 2 ) INFORMATION FOR SEQ ID NO:6:

( i ) SEQUENCE CHARACTERISTICS:
( A ) LENGTH: 651 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: tolworthi
( C ) INDIVIDUAL ISOLATE: 43F ( v i i ) IMMEDIATE SOURCE:
( B ) CLONE: E. coli XL1-Blue (pM1,98- 4), NRRL B-18291

( i x ) FEATURE:
( A ) NAME/KEY: Protein
( B ) LOCATION: 1..651

( x i ) SEQUENCE DESCRIPTION: SEQ ID NO:6:

Met Asn Pro Asn Asn Arg Ser Glu Tyr Asp Thr Ile Lys Val Thr Pro
1 5 10 15

Asn Ser Glu Leu Pro Thr Asn His Asn Gln Tyr Pro Leu Ala Asp Asn
20 25 30

Pro Asn Ser Thr Leu Glu Glu Leu Asn Tyr Lys Glu Phe Leu Arg Met
35 40 45

Thr Ala Asp Asn Ser Thr Glu Val Leu Asp Ser Ser Thr Val Lys Asp
50 55 60

Ala Val Gly Thr Gly Ile Ser Val Val Gly Gln Ile Leu Gly Val Val
65 70 75 80

Gly Val Pro Phe Ala Gly Ala Leu Thr Ser Phe Tyr Gln Ser Phe Leu
85 90 95

Asn Ala Ile Trp Pro Ser Asp Ala Asp Pro Trp Lys Ala Phe Met Ala
100 105 110

Gln Val Glu Val Leu Ile Asp Lys Lys Ile Glu Glu Tyr Ala Lys Ser
115 120 125

Lys Ala Leu Ala Glu Leu Gln Gly Leu Gln Asn Asn Phe Glu Asp Tyr
130 135 140

Val Asn Ala Leu Asp Ser Trp Lys Lys Ala Pro Val Asn Leu Arg Ser
145 150 155 160

Arg Arg Ser Gln Asp Arg Ile Arg Glu Leu Phe Ser Gln Ala Glu Ser
165 170 175

His Phe Arg Asn Ser Met Pro Ser Phe Ala Val Ser Lys Phe Glu Val
180 185 190

Leu Phe Leu Pro Thr Tyr Ala Gln Ala Ala Asn Thr His Leu Leu Leu
195 200 205

-continued

| | | | | | | | | | | | | | | | |
|---|---|---|---|---|---|---|---|---|---|---|---|---|---|---|---|
| Leu | Lys | Asp | Ala | Gln | Val | Phe | Gly | Glu | Glu | Trp | Gly | Tyr | Ser | Ser | Glu |
| | 210 | | | | | 215 | | | | | 220 | | | | |
| Asp | Ile | Ala | Glu | Phe | Tyr | Gln | Arg | Gln | Leu | Lys | Leu | Thr | Gln | Gln | Tyr |
| 225 | | | | | 230 | | | | | 235 | | | | | 240 |
| Thr | Asp | His | Cys | Val | Asn | Trp | Tyr | Asn | Val | Gly | Leu | Asn | Ser | Leu | Arg |
| | | | | 245 | | | | | 250 | | | | | 255 | |
| Gly | Ser | Thr | Tyr | Asp | Ala | Trp | Val | Lys | Phe | Asn | Arg | Phe | Arg | Arg | Glu |
| | | | 260 | | | | | 265 | | | | | 270 | | |
| Met | Thr | Leu | Thr | Val | Leu | Asp | Leu | Ile | Val | Leu | Phe | Pro | Phe | Tyr | Asp |
| | | 275 | | | | | 280 | | | | | 285 | | | |
| Val | Arg | Leu | Tyr | Ser | Lys | Gly | Val | Lys | Thr | Glu | Leu | Thr | Arg | Asp | Ile |
| | 290 | | | | | 295 | | | | | 300 | | | | |
| Phe | Thr | Asp | Pro | Ile | Phe | Thr | Leu | Asn | Ala | Leu | Gln | Glu | Tyr | Gly | Pro |
| 305 | | | | | 310 | | | | | 315 | | | | | 320 |
| Thr | Phe | Ser | Ser | Ile | Glu | Asn | Ser | Ile | Arg | Lys | Pro | His | Leu | Phe | Asp |
| | | | | 325 | | | | | 330 | | | | | 335 | |
| Tyr | Leu | Arg | Gly | Ile | Glu | Phe | His | Thr | Arg | Leu | Arg | Pro | Gly | Tyr | Ser |
| | | | 340 | | | | | 345 | | | | | 350 | | |
| Gly | Lys | Asp | Ser | Phe | Asn | Tyr | Trp | Ser | Gly | Asn | Tyr | Val | Glu | Thr | Arg |
| | | 355 | | | | | 360 | | | | | 365 | | | |
| Pro | Ser | Ile | Gly | Ser | Asn | Asp | Thr | Ile | Thr | Ser | Pro | Phe | Tyr | Gly | Asp |
| | 370 | | | | | 375 | | | | | 380 | | | | |
| Lys | Ser | Ile | Glu | Pro | Ile | Gln | Lys | Leu | Ser | Phe | Asp | Gly | Gln | Lys | Val |
| 385 | | | | | 390 | | | | | 395 | | | | | 400 |
| Tyr | Arg | Thr | Ile | Ala | Asn | Thr | Asp | Ile | Ala | Ala | Phe | Pro | Asp | Gly | Lys |
| | | | | 405 | | | | | 410 | | | | | 415 | |
| Ile | Tyr | Phe | Gly | Val | Thr | Lys | Val | Asp | Phe | Ser | Gln | Tyr | Asp | Asp | Gln |
| | | | 420 | | | | | 425 | | | | | 430 | | |
| Lys | Asn | Glu | Thr | Ser | Thr | Gln | Thr | Tyr | Asp | Ser | Lys | Arg | Tyr | Asn | Gly |
| | | 435 | | | | | 440 | | | | | 445 | | | |
| Tyr | Leu | Gly | Ala | Gln | Asp | Ser | Ile | Asp | Gln | Leu | Pro | Pro | Glu | Thr | Thr |
| | 450 | | | | | 455 | | | | | 460 | | | | |
| Asp | Glu | Pro | Leu | Glu | Lys | Ala | Tyr | Ser | His | Gln | Leu | Asn | Tyr | Ala | Glu |
| 465 | | | | | 470 | | | | | 475 | | | | | 480 |
| Cys | Phe | Leu | Met | Gln | Asp | Arg | Arg | Gly | Thr | Ile | Pro | Phe | Phe | Thr | Trp |
| | | | | 485 | | | | | 490 | | | | | 495 | |
| Thr | His | Arg | Ser | Val | Asp | Phe | Phe | Asn | Thr | Ile | Asp | Ala | Glu | Lys | Ile |
| | | | 500 | | | | | 505 | | | | | 510 | | |
| Thr | Gln | Leu | Pro | Val | Val | Lys | Ala | Tyr | Ala | Leu | Ser | Ser | Gly | Ala | Ser |
| | | 515 | | | | | 520 | | | | | 525 | | | |
| Ile | Ile | Glu | Gly | Pro | Gly | Phe | Thr | Gly | Gly | Asn | Leu | Leu | Phe | Leu | Lys |
| | 530 | | | | | 535 | | | | | 540 | | | | |
| Glu | Ser | Ser | Asn | Ser | Ile | Ala | Lys | Phe | Lys | Val | Thr | Leu | Asn | Ser | Ala |
| 545 | | | | | 550 | | | | | 555 | | | | | 560 |
| Ala | Leu | Leu | Gln | Arg | Tyr | Arg | Val | Arg | Ile | Arg | Tyr | Ala | Ser | Thr | Thr |
| | | | | 565 | | | | | 570 | | | | | 575 | |
| Asn | Leu | Arg | Leu | Phe | Val | Gln | Asn | Ser | Asn | Asn | Asp | Phe | Leu | Val | Ile |
| | | | 580 | | | | | 585 | | | | | 590 | | |
| Tyr | Ile | Asn | Lys | Thr | Met | Asn | Ile | Asp | Gly | Asp | Leu | Thr | Tyr | Gln | Thr |
| | | 595 | | | | | 600 | | | | | 605 | | | |
| Phe | Asp | Phe | Ala | Thr | Ser | Asn | Ser | Asn | Met | Gly | Phe | Ser | Gly | Asp | Thr |
| | 610 | | | | | 615 | | | | | 620 | | | | |
| Asn | Asp | Phe | Ile | Ile | Gly | Ala | Glu | Ser | Phe | Val | Ser | Asn | Glu | Lys | Ile |

-continued

| | | | | | | | | | | |
|---|---|---|---|---|---|---|---|---|---|---|
| 625 | | | | 630 | | | | | 635 | 640 |
| Tyr | Ile | Asp | Lys | Ile | Glu | Phe | Ile | Pro | Val | Gln |
| | | | | 645 | | | | | 650 | |

*BACILLUS THURINGIENSIS* TOXINS ACTIVE AGAINST SCARAB PESTS

CROSS-REFERENCE TO A RELATED APPLICATION

This is a division of application Ser. No. 08/014,941, filed Feb. 1, 1993, now abandoned, which is a continuation-in-part of application Ser. No. 07/828,430, filed Jan. 30, 1992, now U.S. Pat. 5,115,148, which is a continuation-in-part of application Ser. No. 07/808,316, filed on Dec. 16, 1991, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These often appear microscopically as distinctively shaped crystals. The proteins can be highly toxic to pests and specific in their activity. Certain *B.t.* toxin genes have been isolated and sequenced, and recombinant DNA-based *B.t.* products produced and approved. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988 ] TIBTECH 6:S4–S7). Thus, isolated *B.t.* endotoxin genes are becoming commercially valuable.

Over the past 30 years, commercial use of *B.t.* pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely israelensis and san diego (a.k.a. *B.t.* tenebrionis, a.k.a. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents,* R. M. Wilkins, ed., Taylor and Francis, New York and London, 1990, pp. 245–255). See also Couch, T. L. (1980) "Mosquito Pathogenicity of *Bacillus thuringiensis* var. israelensis," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe a *B.t.* isolate named *Bacillus thuringiensis* var. tenebrionis, which is reportedly active against two beetles in the order Coleoptera. These are the Colorado potato beetle, *Leptinotarsa decemlineata,* and *Agelastica alni.*

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whitely [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli.* U.S. Pat. Nos. 4,797,276 and 4,853,331 disclose *B. thuringiensis* strain san diego (a.k.a.*B.t.* tenebrionis, a.k.a. M-7) which can be used to control coleopteran pests in various environments. U.S. Pat. No. 5,151,363 discloses certain isolates of *B.t.* which have activity against nematodes. Many other patents have issued for new *B.t.* isolates and new uses of *B.t.* isolates. The discovery of new *B.t.* isolates and new uses of known *B.t.* isolates remains an empirical, unpredictable art.

Insects in the family Scarabaeidae (scarabs) constitute a serious pest control problem, especially when destructive larval stage insects infest high value turf found in golf courses, playing fields and lawns. The larvae of many species also attack grains, tuberous crops, and ornamentals. Larvae are called "white grubs" or "chafer grubs" and can be found in decaying organic matter (rotting leaves, manure, etc.) or 2–10 cm. deep in soil where they consume the plant roots. In turf infested areas there can be as many as 30 grubs per square foot. The damage caused by an infestation becomes most apparent in the fall when the third instar grubs are feeding. Adult beetles of some scarab species will feed on a wide variety of vegetative host, damaging foliage, fruit and flowers of woody and herbaceous plants. In the U.S. and Europe, populations of larvae and adults have developed resistance to chemical insecticides such as the organochlorines and DDT.

Several scarab pests are of economic importance. Particularly important pests in the U.S., especially east of the Rockies, but also in the Western States, are the masked chafers, Cyclocephala sp. In the east, the northern masked chafer, *C. borealis,* and the southern masked chafer, *C. immaculata,* are common pests, while, in California, *C. hirta* and *C. pasadenae* are present. Also, in the U.S., especially in the area east of the rockies, infestations of Japanese beetles Popillia sp., May or June beetles Phyllophaga sp., black turfgrass beetles Ataenius sp., European chafers Rhizotrogus sp., tend to necessitate the greatest amount of insecticide treatments. Other important scarab pests in the U.S. can be quite damaging but localized such as with Oriental beetles Anomala sp., hoplia chafers Hoplia sp., green June beetle Cotinis sp., and Asiatic garden beetles Maladera sp. Several scarabs not present in the U.S. are of economic importance in Europe, including rose chafers Cetonia sp., cockchafers Melolontha sp., flower beetles Adoretus sp., and garden chafers Phyllopertha sp. The green June beetles, Cotinis sp., can cause serious damage where populations become abundant. The adults are attracted to ripenine fruit and will devour figs, peaches and other thin skinned fruit while on the tree. Larvae are attracted to decaying organic matter and most commonly become pests in turf or fields which have been fertilized with manure. The feeding and tunnelling of the large larvae can become disruptive. The eastern green June beetle *Cotinis nitida* is present in the mid-western and eastern states, while the green June beetle *C. mutabilis* occurs in many of the western states.

BRIEF SUMMARY OF THE INVENTION

The subject invention concerns novel materials and methods for controlling scarab pests. The materials and methods of the subject invention result from the unexpected discovery that certain *B.t.* isolates have activity against these pests.

More specifically, the methods of the subject invention use *B.t.* microbes, or variants thereof, and/or their toxins, to control scarab pests. Specific *B.t.* microbes useful according to the invention are *B.t.* PS86B1, *B.t.* PS43F, and *B.t.* PS50C. Further, the subject invention also includes the use of variants of the exemplified *B.t.* isolates which have substantially the same scarab-active properties as the specifically exemplified *B.t.* isolates. Such variants would include, for example, mutants. Procedures for making mutants are well known in the microbiological art. Ultraviolet light and nitrosoguanidine are used extensively toward this end.

The subject invention also includes the use of genes from the *B.t.* isolates of the invention which genes encode the scarab-active toxins.

Still further, the invention also includes the treatment of substantially intact *B.t.* cells, or recombinant cells containing the genes of the invention, to prolong the scarab activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

Finally, the subject invention further concerns plants which have been transformed with genes encoding scarab-active toxins.

BRIEF DESCRIPTION OF THE SEQUENCES

SEQ ID NO. 1 is the nucleotide sequence (open reading frame only) of the gene designated 50C(a).

SEQ ID NO. 2 is the predicted amino acid sequence of the toxin 50C(a).

SEQ ID NO. 3 is the nucleotide sequence (open reading frame only) of the gene designated 50C(b).

SEQ ID NO. 4 is the predicted amino acid sequence of the toxin 50C(b).

SEQ ID NO. 5 is the composite nucleotide sequence and deduced amino acid sequence of the gene designated 43F.

SEQ ID NO. 6 is the predicted amino acid sequence of the toxin 43F.

DETAILED DISCLOSURE OF THE INVENTION

The subject invention concerns the use of selected strains of *Bacillus thuringiensis* for the control of scarab pests.

Specific *Bacillus thuringiensis* isolates useful according to the subject invention have the following characteristics in their biologically pure form:

Characteristics of *B.t.* PS50C

Colony morphology—Large colony, dull surface, typical *B.t.*

Vegetative cell morphology—typical *B.t.*

Culture methods—typical for *B.t.*

Flagellar serotyping—PS50C belongs to serotype 18, kumamotoensis.

Crystal morphology—a sphere.

RFLP analysis—Southern hybridization of total DNA distinguishes *B.t.* PS50C from *B.t.*s.d. and other *B.t.* isolates.

Alkali-soluble proteins—SDS polyacrylamide gel electrophoresis (SDS-PAGE) shows a 130 kDa doublet protein.

A comparison of the characteristics of *B. thuringiensis* PS50C (*B.t.* PS50C) to the characteristics of the known *B.t.* strains *B. thuringiensis* var. san diego (*B.t.*s.d.), *B. thuringiensis* PS86B1 (NRRL B-18299), and *B. thuringiensis* var. kurstaki (HD-1) is shown in Table 1.

TABLE 1

Comparison of *B.t.* PS50C, *B.t.* PS86B1, *B.t.s.d.*, and *B.t.* HD-1

| | *B.t.* PS50C | *B.t.s.d.* | *B.t.* PS86B1 | *B.t.* HD-1 |
|---|---|---|---|---|
| Serovar | kumamotoensis | morrisoni | tolworthi | kurstaki |
| Type of inclusion | sphere | square wafer | flat, pointed ellipse, plus sm. inclusions | Bipyramid |
| Size of alkali-soluble proteins by SDS-PAGE | 130 kDa doublet | 72,000<br>64,000 | 75,000<br>68,000<br>61,000 | 130,000<br>68,000 |
| Host range | Coleoptera | Coleoptera | Coleoptera | Lepidoptera |

*B.t.* isolates useful according to the subject invention have been deposited. Also deposited are recombinant microbes comprising the *B.t.* genes of interest.

| Culture | Accession Number | Deposit Date |
|---|---|---|
| *Bacillus thuringiensis* PS86B1 | NRRL B-18299 | February 3, 1988 |
| *Bacillus thuringiensis* PS43F | NRRL B-18298 | February 3, 1988 |
| *E. coli* XL1-Blue (pM1, 98-4) | NRRL B-18291 | January 15, 1988 |
| *Bacillus thuringiensis* PS50C | NRRL B-18746 | January 9, 1991 |
| *E. coli* NM522 (pMYC1638) | NRRL B-18751 | January 11, 1991 |

The cultures are on deposit in the permanent collection of the Northern Research Laboratory, U.S. Department of Agriculture, Peoria, Ill., U.S.A.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Genes and toxins.

The genes and toxins according to the subject invention include not only the full length sequences disclosed herein but also fragments of these sequences, or fusion proteins, which retain the characteristic pesticidal activity of the toxins specifically exemplified herein.

It should be apparent to a person skilled in this art that genes coding for scarab-active toxins can be identified and obtained through several means. The specific genes exemplified herein may be obtained from the isolates deposited at a culture depository as described above. These genes, or portions or variants thereof, may also be constructed synthetically, for example, by use of a gene machine. As used herein, the terms "variants" or "variations" of genes refer to nucleotide sequences which code for the same toxins or which code for equivalent toxins having scarab activity. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from *B.t.* isolates and/or DNA libraries using the teachings provided herein. These "equivalent" toxins and genes are also referred to herein as "variant" toxins or genes. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunoassay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, ff the probe molecule and nucleic acid sample hybridize by forming a strong bond between the two molecules, it can be reasonably assumed that the probe and sample have substantial homology. The prohe's detectable label provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures.

Fragments and mutations of the exemplified toxins, which retain the pesticidal activity of the exemplified toxins, would be within the scope of the subject invention, as would genes which encode such fragments and mutants. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining scarab activity are also included in this definition. As used herein, the phrase "scarab activity" includes activity against scarab larvae as well as other stages of development.

Toxins of the subject invention are specifically exemplified herein by the toxins encoded by the genes designated 50C(a), 50C(b), and 43F. Since these toxins are merely exemplary of the toxins of the subject invention, it should be readily apparent that the subject invention further comprises variant toxins (and nucleotide sequences coding for variant toxins) having the same or essentially the same biological activity against scarab pests of the exemplified toxins. These equivalent toxins will have amino acid homology with a toxin of the subject invention. This amino acid homology will typically be greater than 75%, preferably be greater than 90%, and most preferably be greater than 95%. The amino acid homology will be highest in certain critical regions of the toxins which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant Hosts

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of scarab pests where they will proliferate and be ingested by the pest. The result is a control of this pest. Alternatively, the microbe hosting the toxin gene can be treated under conditions that prolong the activity of the toxin produced in the cell. The treated cell then can be applied to the environment of the target pest. The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the soil. These microorganisms are selected so as to be capable of successfully competing in the soil with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffiuens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of Cells

As mentioned above, *B.t.* or recombinant cells expressing a *B.t.* toxin can be treated to prolong activity in the environment. Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques,* W. H. Freeman and Company, 1967); or a combination of physical (heat) and chemical agents that preserve and prolong the actMty of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of Cells

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations

Formulated bait granules containing an attractant and spores and crystals of the *B.t.* isolates, or recombinant microbes comprising the gene(s) obtainable from the *B.t.* isolates disclosed herein, can be applied to the soft. Formulated product can also be applied as a seed-coating or root treatment or total plant treatment at later stages of the crop cycle.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the scarab, e.g., soil, by spraying, dusting, sprinkling, or the like.

The *B.t.* pesticide of the invention can be applied to the soil to control scarab larvae as follows:

- a granule to the soil
- a granule mixed with sand, which fills holes during aeration of turf
- a granule with a sub-surface applicator upon re-seeding in turf
- a spray to the soil (soil drench)
- a spray following aeration
- a spray applied with sub-surface applicator
- combined with a water holding polymer placed in soil with a sub-surface applicator.

*B.t.* pesticidal treatment for adult scarab pests can be done as follows:

- granules with attractant, dispersed in area where beetles are flying
- attractant bait where beetles can congregate to feed
- as a foliar spray to host plant.

Mutants

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30 C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30 C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30 C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* Isolates and Transformed Hosts

A subculture of the *B.t.* isolates and transformed hosts of the invention can be used to inoculate the following medium, a peptone, glucose, salts medium.

| | |
|---|---|
| Bacto Peptone | 7.50 g/l |
| Glucose | 1.00 g/l |
| $KH_2PO_4$ | 3.40 g/l |
| $K_2HPO_4$ | 4.35 g/l |
| Salt Solution | 5.00 ml/l |
| $CaCl_2$ Solution | 5.00 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30 C. on a rotary shaker at 200 rpm for 64 hours.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes from *B.t.* Isolate PS50C

Total cellular DNA was prepared from *Bacillus thuringiensis* (*B.t.*) cells grown to an optical density, at 600 nm, of 1.0. The cells were recovered by centrifugation and protoplasts were prepared in TES buffer (30 mM Tris-HCl 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4 C. in 100 mM (final concentration) neutral potassium chloride. The supernate was extracted twice with phenol/chloroform (1:1). Nucleic acids were precipitated with ethanol and DNA was purified by isopycnic banding on cesium chloride-ethidium bromide gradients.

Total cellular DNA from *B.t.* subsp. kumamotoensis (*B.t.* kum.), isolate PS50C, was digested with HindIII and fractionated by electrophoresis on a 0.8% (w/v) agarose-TAE (50 mM Tris-HCl, 20 mM NaOAc, 2.5 mM EDTA, pH = 8.0) buffered gel. A Southern blot of the gel was hybridized with a [$^{32}$P]-radiolabeled oligonucleotide probe. Results showed that the hybridizing fragments of PS50C are approximately 12 Kb and 1.7 Kb in size.

A library was constructed from PS50C total cellular DNA partially digested with Sau3A and size fractionated by gel electrophoresis. The 9-23 Kb region of the gel was excised and the DNA was electroeluted and then concentrated using an Elutip-d™ ion exchange column (Schleicher and Schuel, Keene, N.H.). The isolated Sau3A fragments were ligated into BamHI-digested LambdaGEM-11™ (PROMEGA). The packaged phage were plated on *E. coli* KW251 cells (PROMEGA) at a high titer and screened using the radiolabeled oligonucleotide probe. Hybridizing plaques were purified and rescreened at a lower plaque density. Single isolated, purified plaques that hybridized with the probe were used to infect *E. coli* KW251 cells in liquid culture for preparation of phage for DNA isolation. DNA was isolated by standard procedures. Preparative amounts of DNA were digested with XhoI (to release the inserted DNA from lambda sequences) and separated by electrophoresis on a 0.6% agarose-TAE gel. The large fragments were purified by ion exchange chromatography as above and ligated to XhoI-digested, dephosphorylated pHTBlueII (an *E. coli/B. thuringiensis* shuttle vector comprised of pBluescript s/k [Stratagene] and the replication origin from a resident *B.t.* plasmid [D. Lereclus et al. (1989) FEMS *Microbiology Letters* 60:211–218]). The ligation mix was introduced by transformation into competent *E. coli* NM522 cells (ATCC 47000) and plated on LB agar containing ampicillin, isopropyl-(β)-D-thiogalactoside (IPTG) and 5-bromo-4-chloro-4-indolyl-(β)-D-galactoside (XGAL). White colonies, with putative restriction fragment insertions in the (β)-galactosidase gene of pHTBlueII, were subjected to standard rapid plasmid purification procedures. Plasmids were analyzed by XhoI digestion and agarose gel electrophoresis. The desired plasmid construct, pMYC1638, contains an approximately 12 Kb XhoI insert. A partial restriction map of the cloned insert indicates that the toxin gene is novel compared to the maps of other toxin genes encoding insecticidal proteins. The nucleotide sequence (open reading frame only), which has been designated 50C(a) is shown in SEQ ID NO. 1. The predicted peptide sequence of the toxin is shown in SEQ ID NO. 2.

Plasmid pMYC1638 was introduced into an acrystalliferous (Cry⁻) *B.t.* host (HD-1 cryB obtained from A. Aronson, Purdue University) by electroporation. Expression of an approximately 130 kDa protein was verified by SDS-PAGE.

Plasmid pMYC1638 containing the *B.t.* toxin gene, can be removed from the transformed host microbe by use of standard well-known procedures. For example, *E. coli* NM522[pMYC1638] NRRL B-18751 can be subjected to cleared lysate isopycnic density gradient procedures, and the like, to recover pMYC1638.

A second gene, designated 50C(b), has also been cloned and sequenced from PS50C. The nucleotide sequence for 50C(a) is shown in SEQ ID NO. 3, and the predicted amino acid sequence for this toxin is shown in SEQ ID NO. 4.

EXAMPLE 3

Cloning of Toxin Gene From *B.t.* Isolate PS43F and Transformation into Pseudomonas Total cellular DNA was prepared by growing the cells of *B.t.* isolate PS43F and M-7 to a low optical density ($OD_{600}$= 1.0) and recovering the cells by centrifugation. The cells were protoplasted in a buffer containing 20% sucrose and 50 mg/ml lysozyme. The protoplasts were lysed by addition of SDS to a final concentration of 4%. The cellular material was precipitated overnight at 4 C. in 100 mM neutral potassium chloride. The supernate was phenol/chloroform extracted twice and the DNA precipitated in 68% ethanol. The DNA was purified on a cesium chloride gradient. DNAs from strains 43F and M-7 (as a standard of reference) were digested with EcoRI and run out on a 0.8% agarose gel. The gel was Southern blotted and probed with the nick translated ORF XmnI to PstI fragment of the toxin encoding gene isolated from M-7 (this will be subsequently referred to as Probe). The results showed 43F to hybridize to Probe at 7.5 kb which is different than the standard.

Preparative amounts of 43F DNA were digested with EcoRI and run out on a 0.8% agarose gel. The 7.5 kb region of the preparative gel was isolated and the DNA electroeluted and concentrated using an ELUTIP™-d (Schleicher and Schuell, Keene, N.H.) ion exchange column. A sample was blotted and probed to verify the fragment was indeed isolated. The 7.5 kb EcoRI fragment was ligated to Lambda ZAP™ EcoRI arms. The packaged recombinant phage were plated out with *E. coli* strain BB4 (Stratagene Cloning Systems, La Jolla, Calif.) to give high plaque density.

The plaques were screened by standard procedures with Probe. The plaques that hybridized were purified and rescreened at a lower plaque density. The resulting phage were grown with M13 helper phage (Stratagene) and the recombinant BLUESCRIPT™ plasmid was automatically excised and packaged. The "phagemid" was re-infected in XL1-blue *E. coli* cells (Stratagene) as part of the automatic excision process. The infected XL1-blue cells were screened for ampicillin resistance and the resulting colonies were miniprepped to find the desired plasmid pM1,98-4. The recombinant *E. coli* XL1-Blue (pM1,98-4) strain is called MR381.

The plasmid pM1,98-4 contained a 7.5 kb EcoRI insert. To verify that this insert was the one of interest, a Southern blot was performed and probed. The 7.5 kb band hybridized with Probe, confirming that the fragment had been cloned. Restriction endonuclease analysis of the 7.5 kb EcoRI fragment with the enzymes HindIII, PstI, SpeI, BamHI and XbaI was done to show that a gene different from M-7 had been cloned. The enzymes which cut inside the 7.5 kb EcoRI fragment were HindIII (twice) SpeI (twice) and PstI (once). The open reading frame (ORF) of the 43F gene cut once with HindIII, twice with SpeI and did not cut with XbaI, EcoRI, or BamHI. The nucleotide sequence for the 43F gene is shown in SEQ ID NO. 5 and the predicted amino acid sequence for this toxin is provided in SEQ ID NO. 6.

The cloned toxin gene from PS43F can be modified for expression in *P. fluorescens* in the following way:

(1) A plasmid containing the Ptac-promoted cryIA(b)-like toxin gene can be made using a 3-way ligation invoMng the Ptac promoter and toxin gene on a BamHI-PstI fragment of about 4500 bp from pM3,130-7 (from MR420, NRRL B-18332, disclosed in U.S. Pat. No. 5,055,294), a NotI-BamHI fragment of about 5500 bp from pTJS260 (containing the tetracycline resistance genes, available from Dr. Donald Helinski, U.C. San Diego), and a NotI-PstI fragment of about 6100 bp from pTJS260 (containing the replication region). The assembled plasmid is recovered following transformation of *E. coli* and growth under tetracycline selection.

(2) A plasmid containing the Ptac-promoted 43F toxin gene can be made by ligating the toxin gene-containing FspI-SspI fragment of about 2200 bp from pM1,98-4 (from MR381(pM1,98-4), NRRL B-18291) into the SmaI site of the *E. coli* vector, pKK223-3 (Pharmacia). The Ptac-promoted 43F toxin plasmid can be recovered following transformation of *E. coli,* growth under ampicillin selection, and screening for plasmids with inserts in the proper orientation for expression from the tac promoter by techniques well known in the art.

(3) The Ptac-promoted 43F toxin can be assembled into, for example, the pTJS260-derived vector in a three-way ligation using the 12.6 kb DNA fragment having BamHI and filled-in NsiI ends from the plasmid resulting from step 1 above, to the BamHI-NsiI Ptac-containing fragment of about 1.2 kb and the NsiI-ScaI fragment of about 2.1 kb containing the 3 end of the 43F toxin gene and adjacent vector DNA from the plasmid resulting from step 2 above.

The resulting pTJS260-derived 43F toxin expression plasmid can be introduced into *Pseudomonas fluorescens* by electroporation.

The above cloning procedures were conducted using standard procedures unless otherwise noted.

The various methods employed in the preparation of the plasmids and transformation of host organisms are well known in the art. These procedures are described in Maniatis, T., E. F. Fritsch, J. Sambrook (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Boehringer Mannheim, Indianapolis, Ind., or New England BioLabs, Beverly, Mass. The enzymes were used according to the instructions provided by the supplier.

Plasmid pM1,98-4 containing the *B.t.* toxin gene, can be removed from the transformed host microbe by use of standard well-known procedures. For example, *E. coli* XL1-Blue (pM1,98-4) can be subjected to cleared lysate isopycnic density gradient procedures, and the like, to recover pM1,98-4.

EXAMPLE 4

Testing of *B.t.* PS86B1 and Transformed Hosts

Third instar Pasadena Masked Chafers, *Cyclocephala pasadenae,* were found to be susceptible to the *B.t.* isolate PS86B1 as well as a *Pseudomonas fluorescens* transformed host containing the δ-endotoxin expressing gene obtained from *B.t.* PS43F. In the bioassays, larvae were fed an aqueous suspension of the material mixed with ryegrass roots. Larvae were held with the treated diet at room temperature in 1 oz. plastic cups, and observed for mortality by prodding. Dosages of PS86B1 and the *Pseudomonas fluorescens* transformed host greater than 500 ppm (δ-endotoxin protein/diet) gave 80% control in 15 days.

EXAMPLE 5

Testing of *B.t.* Transformed Host Containing a δ-Endotoxin Gene from PS50C

The transformed host was prepared by introducing plasmid pMYC1638 (NRRL B-18751), containing the δ-endotoxin expressing gene obtained from *B.t* PS50C, into an acrystalliferous ($cry^-$) *B.t.* host (HD-1 cryB obtained from A. Aronson, Purdue University) by standard electroporation procedures.

Larvae of Cotinis sp. were found to be susceptible to the transformed host containing the δ-endotoxin expressing gene obtained from the *B.t.* isolate PS50C. The larvae were fed an aqueous suspension of the transformed host mixed with peat moss. The larvae were held at room temperature in 1 oz. plastic cups with the treated peat, and checked regularly during the assays for mortality. Dosages of the transformed host of 750 ppm (δ-endotoxin/diet) caused 90% mortality of the larvae by day 13. In addition, the transformed host was shown to affect all three instar stages of the larvae.

EXAMPLE 6

Testing of *B.t.* PS86B1 Against *Cyclocephala borealis*

Third instar Northern Masked Chafer *Cyclocephala borealis* were found to be susceptible to the *B.t.* isolate PS86B1. Larvae were fed Kentucky bluegrass roots which had been dipped in a *B.t.* suspension. Larvae were held at room temperature in 1 oz. cups containing the treated roots and observed for mortality by prodding. Dosages greater than 500 ppm (protein/diet) gave 79% control in 7 days.

EXAMPLE 7

Testing of *B.t.* PS86B1 Against *Popillia japonica*

Third instar Japanese beetle *Popillia japonica* were found to be susceptible to the *B.t.* isolate PS86B1. Larvae were fed a *B.t.* suspension mixed with compost. Larvae were held with the treated compost at room temperature in 1 oz. plastic cups and observed for mortality by prodding. Dosages of PS86B1 greater than 500 ppm (protein/diet) gave greater than 40% control in 7 days.

EXAMPLE 8

Insertion of Toxin Genes Into Plants

One aspect of the subject invention is the transformation of plants with genes encoding a scarab-active toxin. The transformed plants are resistant to attack by scarab pests.

Genes encoding scarab-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the fight and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electropotation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 9

Cloning of Novel *B.t.* Genes into Insect Viruses

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotid encoding a toxin which is active against scarab pests, said polynucleotide encoding the amino acid sequence of SEQ ID NO. 4 or a fragment thereof sufficient to retain anti-scarab activity.

2. An isolated polynucleotide, according to claim 1, comprising the nucleotide sequence of SEQ ID NO. 3 or a fragment thereof sufficient to encode a toxin having activity against scarab pests.

3. A toxin which is active against scarab pests, said toxin comprising the amino acid sequence of SEQ ID No. 4 or a fragment thereof sufficient to retain anti-scarab activity.

4. A microbe transformed by a polynucleotide sequence of claim 1.

* * * * *

UNITED STATES PATENT AND TRADEMARK OFFICE

CERTIFICATE OF CORRECTION

PATENT NO. : 5,554,534

DATED : September 10, 1996

INVENTOR(S) : Tracy E. Michaels, Kenneth E. narva, and Luis Foncerrada

It is certified that error appears in the above-indentified patent and that said Letters Patent is hereby corrected as shown below:

Column 1: Line 65: "CryII" should read --CryII--; Line 66: "CryIII" should read --CryIII--.
Column 2: Line 55: "ripenine" should read --ripening--.
Column 5: Line 66: "ff" should read --if--.
Column 6: Line 3: "prohe's" should read --probe's--.
Column 7: Line 52: "diffiuens" shoudl read --diffluens--.
Column 8: Line 33: "actMty" should read --activity--.
Column 9: Line 22: "soft" should read --soil--.
Column 11: Line 28: "HindIII" should read --HindIII--.
Column 13: Line 6: "HindIII" should read --HindIII--; Line 9: "HindIII" should read --HindIII--; Line 11: "HindIII" should read --HindIII--; Line 18: "invoMng" should read --involving--.
Column 14: Line 31: "(cry$^{-)}$" should read --(cry$^{-}$)--.
Column 15: Line 53: "Agrobacteriurn" should read --Agrobacterium--.
Column 16: Line 10: "fight" should read --right--; Line 27: "elecrtropotation" should read --electroporation--.
Column 45: Line 9: "polynucleotid" should read --polynucleotide--.

Signed and Sealed this

Twentieth Day of May, 1997

Attest:

Bruce Lehman

BRUCE LEHMAN

Attesting Officer

*Commissioner of Patents and Trademarks*